United States Patent
Chang et al.

(10) Patent No.: US 6,969,706 B1
(45) Date of Patent: Nov. 29, 2005

(54) PRESERVED PHARMACEUTICAL COMPOSITIONS COMPRISING CYCLODEXTRINS

(75) Inventors: Chin-Ming Chang, Tustin, CA (US); James Chang, Newport Beach, CA (US); Robert T. Lyons, Laguna Hills, CA (US)

(73) Assignee: Allergan, Inc., Irvine, CA (US)

( * ) Notice: Subject to any disclaimer, the term of this patent is extended or adjusted under 35 U.S.C. 154(b) by 54 days.

(21) Appl. No.: 10/844,647

(22) Filed: May 12, 2004

(51) Int. Cl.$^7$ .......................................... A61K 31/724
(52) U.S. Cl. ........................ 514/60; 514/912; 514/914; 514/970; 536/103
(58) Field of Search .......................... 514/58, 839, 60, 514/912, 914, 970; 536/103

(56) References Cited

U.S. PATENT DOCUMENTS

| | | | |
|---|---|---|---|
| 3,459,731 A | | 8/1969 | Gramera |
| 4,960,799 A | * | 10/1990 | Nagy .......................... 514/567 |
| 5,800,807 A | | 9/1998 | Hu |
| 5,985,310 A | | 11/1999 | Castillo et al. |
| 5,998,488 A | * | 12/1999 | Shinohara et al. .......... 424/658 |
| 6,358,935 B1 | * | 3/2002 | Beck et al. .................... 514/58 |
| 6,407,079 B1 | | 6/2002 | Muller et al. |
| 6,576,649 B1 | * | 6/2003 | Kis ............................. 514/324 |
| 6,656,923 B1 | * | 12/2003 | Trinh et al. .................... 514/58 |
| 2002/0198174 A1 | | 12/2002 | Lyons |
| 2004/0214797 A1 | * | 10/2004 | Lyons et al. .................. 514/58 |

OTHER PUBLICATIONS

Loftsson et al, Drug Development and Industrial Pharmacy, 1992, 18 (13), pp. 1477-1484.
Simpson, Fems, Microbiology Letters, 90, pp. 197-200 (1992).
Miyajima et al, Chem. Pharm. Bull., 35(1), 389-393.
Chun, "Inclusion complexation of hydrocortisone butyrate . . . " International Journal of Pharmaceutics, 96 (Jul. 31), pp. 91-103.
Vianna et al, (1998), "Formation of cyclodextrin inclusion complexes with corticosteroids . . . " International Journal of Pharmaceutics, 167 (Jun. 1), pp. 206-213.

* cited by examiner

Primary Examiner—James O. Wilson
Assistant Examiner—Jason H. Johnsen
(74) Attorney, Agent, or Firm—Brent A. Johnson; Martin A. Voet; Robert J. Baran

(57) ABSTRACT

A composition comprising a cyclodextrin, a guanidine-based cationic compound, and sorbic acid is disclosed herein. Preservatives and methods related thereto, and experimental results suggesting certain advantages related to these compositions, preservatives, and methods are also presented herein.

23 Claims, No Drawings

PRESERVED PHARMACEUTICAL COMPOSITIONS COMPRISING CYCLODEXTRINS

BACKGROUND OF THE INVENTION

1. Field of the Invention

The present invention relates to pharmaceutical compositions. In particular, the present invention relates to compositions comprising cyclodextrins.

2. Description of the Related Art

Cyclodextrins are cyclic oligosaccharides containing 6, 7, or 8 glucopyranose units, referred to as α-cyclodextrin (structure depicted below), β-cyclodextrin, or γ-cyclodextrin respectively, which are often used in pharmaceutical formulations.

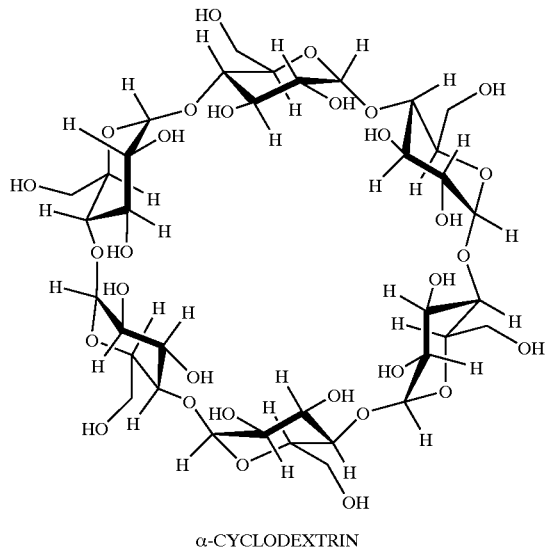

α-CYCLODEXTRIN

Cyclodextrins have a hydrophilic exterior, which makes them water-soluble, and a hydrophobic interior which forms a cavity. In an aqueous environment, hydrophobic portions of molecules often enter the hydrophobic cavity of cyclodextrin to form inclusion compounds. Although inclusion compounds are often formed between cyclodextrins and hydrophobic molecules, cyclodextrins are also capable of other types of nonbonding interactions with molecules that are not inside the hydrophobic cavity. Cyclodextrins have three free hydroxyl groups for each glucopyranose unit, or 18 hydroxyl groups on α-cyclodextrin, 21 hydroxyl groups on β-cyclodextrin, and 24 hydroxyl groups on γ-cyclodextrin. One or more of these hydroxyl groups can be reacted with any of a number of reagents to form a large variety of cyclodextrin derivatives. Some of the more common derivatives of cyclodextrin are hydroxypropyl ethers, sulfonates, and sulfoalkylethers.

In pharmaceutical formulations, cyclodextrins and cyclodextrin derivatives are often used to improve the solubility of a drug. While inclusion compounds are involved in many cases of enhanced solubility, other interactions between cyclodextrins and insoluble compounds can also improve solubility. As mentioned, the use of cyclodextrins in pharmaceutical compositions is well known in the art. For example, U.S. Pat. No. 6,407,079 teaches the use of β-cyclodextrin derivatives to form inclusion compounds that improve the solubility of the drug.

Cyclodextrin derivatives have been demonstrated to be useful in solubilizing lipophilic or water-insoluble therapeutic agents or drugs. For example, U.S. Pat. No. 5,472,954 discloses the use of hydroxypropylmethylcellulose and hydroxypropyl cyclodextrins to solubilize hydrocortisone. The use of cyclodextrin and cyclodextrin derivatives in ophthalmic formulations is also known. For example, U.S. 2002/0198174 discloses a composition comprising "cyclodextrin", "prednisolone acetate", and "PHMB (1 ppm)" among other components, and EP 0435682 A2 teaches the use of cyclodextrins in ophthalmic compositions with prostaglandins to treat ocular hypertension.

Antimicrobial preservation of cyclodextrin-containing formulations can present special problems. For example, Loftsson et al., Drug Development and Industrial Pharmacy, 18 (13), 1477–1484 (1992), have investigated interactions between several commonly used preservatives and 2-hydroxypropyl-β -cyclodextrin (HPβCD). Loftsson et al. reported that the antimicrobial activity of the preservative can be reduced by the formation of preservative-cyclodextrin inclusion complexes, specifically chlorobutanol, methylparaben, propylparaben, had significantly reduced preservative activity for a number of pathogens, and it was shown that chlorobutanol reduces the solubilizing effects of HPβCD on hydrocortisone, prednisolone, and triamcinolone. However, benzalkonium chloride and chlorhexidine gluconate did possess preservative activity in HPβCD solutions. Additionally, Simpson, FEMS Microbiology Letters, 90, 197–200 (1992), reported that cyclodextrins can inactivate the antimicrobial activity of certain quaternary ammonium compounds. See also, Miyajima et al., Chem. Pharm. Bull., 35(1), 389–393 (1987), regarding the interaction of short-chain alkylammonium salts with cyclodextrins in aqueous solutions, which concluded that α-, β-, and γ-cyclodextrins form complexes with alkylammonium salts having alkyl groups longer than n-butyl, n-hexyl, and n-decyl, respectively.

JP 60149530 A (Takeda Chem. Ind., Ltd.) discloses aqueous compositions of a principal agent and a cyclodextrin where the compositions contain as a preservative a chlorhexidine derivative of the formula

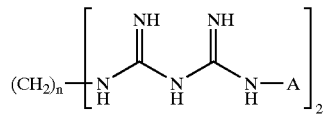

where A is [independently] (un)substituted phenyl; n is 3–9; and the polymethylene chain may be interrupted by an oxygen atom or an aromatic ring.

JP 01016728 A (Santen Seiyaku KK) discloses antiseptic aqueous preparations containing a drug, a cyclodextrin and a cationic surfactant as a preservative. By adding a cyclodextrin or cyclodextrin derivative, cationic surfactants commonly incompatible with certain drugs can be combined. Disclosed cationic surfactants are benzalkonium chloride, benzethonium chloride or chlorohexidine gluconate. Disclosed drugs include sodium hyaluronate, pilocarpine hydrochloride, lysosyme chloride, $Na_2$ chondroitin sulfate, glycyrrhetinate, pirenoxine, sodium chromoglycate, and dimethylisopropylazulene sodium sulfate.

JP 6016547 A (Wakamoto Pharm. Co. Ltd.) discloses eye drop compositions containing diclofenac sodium and a water soluble cyclodextrin compound. The reference also discloses that these compositions can be preserved using benzalkonium chloride, benzethonium chloride and chlorhexidine gluconate as cationic surfactants; methylparaben, ethylparaben, propylparaben and butylparaben as parabens; and phenylethyl alcohol and benzyl alcohol as alcohols.

U.S. Pat. No. 5,998,488 discloses "The ophthalmic composition of the invention contains (1) an antimicrobial preservative having a cationic group, (2) a cyclodextrin, (3) ethylenediaminetetraacetic acid or a salt thereof, and (4) boric acid and/or borax as essential components." This patent also discloses that "The antimicrobial preservative having a cationic group used herein may be selected from well-known antimicrobial preservatives, for example, quaternary ammonium salts such as benzalkonium chloride, benzethonium chloride, cetyldimethylbenzylammonium chloride, domiphen bromide, 3-(trimethoxysilyl)propyldimethyloctadecylammonium chloride, stearyldimethylbenzylammonium chloride, stearyltolylmethyl-ammonium chloride, distearyldimethylammonium chloride, stearylpentaethoxyammonium chloride, cetylpyridinium chloride, cetylpyridinium bromide, and lauroylisoquinolium bromide; and guanidines such as chlorohexidine hydrochloride, chlorohexidine gluconate, dodecylguanidine hydrochloride, polyhexmethylenebiguanidine hydrochloride, and 6-acetoxy-2,4-dimethylmetadioxane." However, the patent further states "benzalkonium chloride is most effective and preferable."

In citing the foregoing references, and other references cited herein, applications make no admission as to whether any of said references constitutes prior art. Rather, the determination of what constitutes prior art is a legal exercise made on the basis of the dates said references were made available to the public, the authors or inventors of said references, and the effective filing date of the disclosure made herein.

BRIEF DESCRIPTION OF THE INVENTION

A composition comprising a cyclodextrin, a guanidine-based cationic compound, and sorbic acid is disclosed herein.

A preservative for cyclodextrin-containing ophthalmic compositions comprising a guanidine-based cationic compound and sorbic acid is also disclosed herein.

A method comprising providing an ophthalmic composition comprising a cyclodextrin with an effective amount of a guanidine-based cationic compound and an effective amount of sorbic acid, wherein said method prevents, attenuates, or reduces the pathogenic contamination of said composition.

DETAILED DESCRIPTION OF THE INVENTION

While not intending to be limited or bound in any way by theory, we have surprisingly discovered that the combination of sorbic acid or sorbate and guanidine-based cationic compounds is particularly useful in preserving compositions comprising one or more cyclodextrins. The term "cyclodextrin" as disclosed herein should be interpreted broadly to include the natural cyclodextrins and their derivatives, including the alkylated and hydroxyalkylated derivatives and the branched cyclodextrins. Cyclodextrins and their derivatives which have been previously described as useful for complexation with drugs are of particular interest herein. In addition to α-, β- and γ-cyclodextrin, the ether and mixed ether derivatives and those derivatives bearing sugar residues are of special interest. Especially useful herein are the hydroxyethyl, hydroxypropyl (including 2- and 3-hydroxypropyl) and dihydroxypropyl ethers, their corresponding mixed ethers and further mixed ethers with methyl or ethyl groups, such as methyl-hydroxyethyl, ethyl-hydroxyethyl and ethyl-hydroxypropyl ethers of α-, β- and γ-cyclodextrin. Hydroxypropyl-α-cyclodextrin and its preparation by propylene oxide addition to β-cyclodextrin, and hydroxyethyl-β-cyclodextrin and its preparation by ethylene oxide addition to β-cyclodextrin, were described in a patent of Gramera et al. (U.S. Pat. No. 3,459,731, issued August 1969) over 20 years ago. Other useful cyclodextrin derivatives are maltosyl, glucosyl and maltotriosyl derivatives of β- and γ-cyclodextrin, which may contain one or more sugar residues, e.g. glucosyl or diglucosyl, maltosyl or dimaltosyl, as well as various mixtures thereof, e.g. a mixture of maltosyl and dimaltosyl derivatives. Other useful cyclodextrin derivatives comprise anionic functional groups such as sulfobutylether derivatives, sulfonates, phosphates, and the like. Specific examples of cyclodextrin derivatives for use herein include hydroxypropyl-β-cyclodextrin, hydroxypropyl-γ-cyclodextrin, sulfobutylether-β-cyclodextrin, and sulfobutylether-γ-cyclodextrin, as well as hydroxyethyl-β-cyclodextrin, hydroxyethyl-γ-cyclodextrin, dihydroxypropyl-β-cyclodextrin, glucosyl-β-cyclodextrin, diglucosyl-β-cyclodextrin, maltosyl-β-cyclodextrin, maltosyl-γ-cyclodextrin, maltotriosyl-β-cyclodextrin, maltotriosyl-γ-cyclodextrin and dimaltosyl-β-cyclodextrin, and mixtures thereof such as maltosyl-β-cyclodextrin/dimaltosyl-α-cyclodextrin. Procedures for preparing such cyclodextrin derivatives are well-known, for example, from Bodor U.S. Pat. No. 5,024,998, dated Jun. 18, 1991, expressly incorporated herein by reference, and references cited therein.

The amount of cyclodextrin used in the compositions disclosed here is dependent upon the particular situation, and can vary. While not intended to limit the scope of the invention in any way, in many compositions the concentration of cyclodextrin is from 0.1% to 40%. In other compositions, the cyclodextrin concentration is from 10% to 30%. In some compositions, the cyclodextrin concentration is about 20%.

A "guanidine-based cationic compound" is a compound which comprises a guanidine unit having the structure shown below, where the lines attached to the saturated nitrogen atoms represent bonds to a nitrogen or carbon atom. The guanidine-based cationic compound has one or more cationic centers in that one or more of the nitrogen atoms of a guanidine unit is protonated.

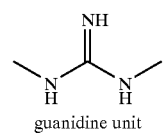

guanidine unit

Oligomeric and polymeric cationic compounds based upon guanidine are often used as preservatives in ophthalmic compositions. One oligomeric guanidine-based cationic compound is chlorhexidine, which has the structure shown below. In the pH range used in ophthalmic compositions, one or more of the nitrogen atoms is protonated, and the compound is thus generally cationic.

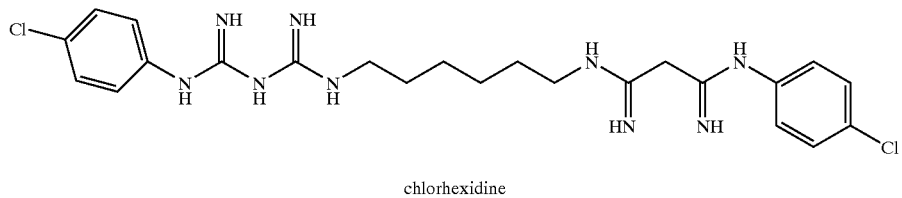

chlorhexidine

One polymeric guanidine-based cationic compound is polyhexamethylene biguanide (PHMB), also known as polyaminopropyl biguanide and polihexanide, which has the structure shown below. In the pH range used in ophthalmic compositions, one or more of the nitrogen atoms is protonated, and the compound is thus generally cationic. Other guanidine-based cationic compounds, such as dodecylguanidine, are also known. One commercially available form of PHMB is known by the tradename COSMOCIL® CQ, manufactured by [Avecia, Inc., Wilmington, Del.], which is sold as a 20% aqueous solution of PHMB HCl having a molecular weight of 2500±300, and an average n (structure) of 10–13. PHMB HCl is the hydrochloride salt of PHMB, where there are n HCl species per molecule.

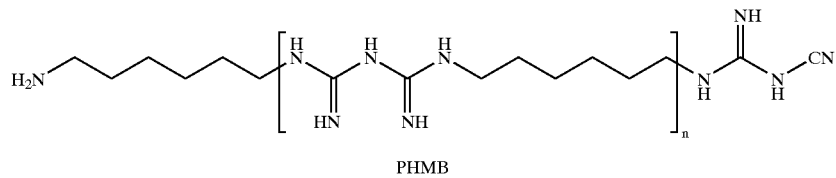

PHMB

An effective amount of the guanidine-based cationic compound can be readily determined by a person having ordinary skill in the art. This amount can vary, depending upon the particular composition in which it is used. In certain compositions, the concentration of the guanidine-based cationic compound is from about 0.1 ppm to 25 ppm. In other compositions, the concentration is from 1 ppm to 5 ppm. In other compositions, the concentration is from 3 to 5 ppm.

The term "sorbic acid" as used herein, applies to both sorbic acid and sorbate salts. Thus, sodium sorbate, potassium sorbate, ammonium sorbate, or any salt of sorbic acid could be used in the methods and compositions disclosed herein and should be interpreted to mean "sorbic acid" as indicated by the claims herein. It is understood that in an aqueous solution having a pH of 7, sorbic acid, which has a $pK_a$ of 4.76 will be essentially completely deprotonated. Thus, the actual form of sorbic acid in a composition may be different than that which was added to the composition, and the term "sorbic acid" should be applied as broadly as generally understood in the art in light of these considerations. In a case where a mass-dependent concentration is given for sorbic acid, the concentration is defined as the concentration of the neutral form of sorbic acid, regardless of what form is added, or what form is actually present in the composition. An effective concentration of the sorbic acid can be readily determined by a person of ordinary skill in the art, and can vary. In certain compositions, the concentration of sorbic acid is between 0.05% and 5%. In other compositions, the concentration of sorbic acid is from 0.05% to 1%. Other compositions comprise from 0.05% to 0.4% sorbic acid. Other compositions comprise about 0.6% sorbic acid.

The term "preservative" as used herein, refers broadly to any excipient, or combination of excipients, which is effective in preventing, attenuating, or reducing the pathogenic contamination of said composition microbial or pathogenic contamination in an ophthalmic composition. In other words, a preservative might kill pathogens that are present in a composition; prevent the growth of one or more pathogens; attenuate, or reduce, the rate of growth of one or more pathogens; or a combination of these. Standard tests of antimicrobial effectiveness exists for various government organizations including the United States Food and Drug Administration's USP test, and the European Union's Ph Eur-A and Ph Eur-B tests. Tests are often carried out on standard microbial species such as Staphylococcus aureus, Pseudomonas aeruginosa, Escherichia coli, Candida albicans, and Aspergillus niger.

Certain embodiments disclosed herein comprise a therapeutically active agent. A therapeutically active agent is a compound which is useful in the treatment or prevention of a disease or any undesirable condition. Some examples of therapeutically active agents useful in ophthalmic compositions include, without limitation, ciprofloxacin, ofloxacin, norfloxacin, cefazolin, tobramycin, gentamycin, an aminoglycoside, a penicillin, a semi-synthetic penicillin, amoxicillin, ampicillin, carbenicillin, ticarcillin, mezlocillin, a cephalosporin, vancomycin, chloramphenicol, erythromycin, clindamycin, rifampin, bacitracin, polymyxin, spectinomycin, a sulfonamide, trimethoprim, super oxide dismutase, astaxanthin, canthazanthin, beta-carotene, zeaxanthin, lutein, alpha-tocopherol, ascorbic acid, glutathione, selenous acid, sodium selenate, acyclovir, ganciclovir, idoxuridine, vidarabine, trifluridine, bromovinyldeoxyuridine, azidothymidine, amantadine, rimantadine, dexamethasone, prednisolone, prednisone, fluorometholone, betamethasone, hydrocortisone, an α-hydroxyacid, a β-hydroxyacid, an α-ketoacid, a β-ketoacid, ketorolac, indomethacin, flurbiprofen, loxoprofen, diclofenac, atropine, pilocarpine, carbachol, physostigmine, phenylephrine, acetazolamide, timolol maleate, fibronectin and vitronectin as well as analogs or fragments thereof, acetyl cysteine, or mixtures thereof.

In one embodiment, the therapeutically active agent is a steroid such as an estrogen; a glucocorticoid; a progestin; a mineralocorticoid; a corticosteroid, such as cortisone, hydrocortisone, prednisone, prednisolone, methylprednisone, triamcinolone, fluoromethalone, dexamethasone, medrysone, betamethasone, loteprednol, fluocinolone, flumethasone, or mometasone; or an androgen such as testosterone, methyltestosterone, or danazol.

In other embodiments, the therapeutically active agent is selected from the group comprising prostaglandins such as latanoprost, travoprost, unoprostone isopropyl, and the like; prostamides, such as bimatoprost; retinoids such as tazarotene, tretinoin, isotretinoin, or the like; α-adrenergic agonists, such as brimonidine; tyrosine kinase inhibitors; and steroids.

In another embodiment, the therapeutically active agent is a prostamide or a prostaglandin.

In ophthalmic compositions, a chelating agent may be used to enhance preservative effectiveness. Suitable chelating agents are those known in the art, and, while not intending to be limiting, edetate (EDTA) salts like edetate disodium, edetate calcium disodium, edetate sodium, edetate trisodium, and edetate dipotassium are examples of useful chelating agents. It is understood that EDTA refers to a species having four carboxylic acid functional groups, and that these carboxylic acid groups may be protonated or deprotonated (i.e. in the salt form) depending upon the pH of the composition it is in.

As is known in the art, buffers are commonly used to adjust the pH to a desirable range for ophthalmic use. Generally, a pH of around 5–8 is desired, however, this may need to be adjusted due to considerations such as the stability or solubility of the therapeutically active agent or other excipients. In compositions comprising prednisolone acetate, a pH of from 4 to 6 may help to stabilize the compound. Other prednisolone acetate containing compositions have a pH of from 4.5 to 5.5. Other prednisolone acetate containing compositions have a pH of about 4.5.

Many buffers including salts of inorganic acids such as phosphate, borate, and sulfate are known. When the concentration of a buffer is given, it refers to the total concentration of the buffering species. In other words, if a concentration contains 0.01 M bisulfate and 0.01 M sulfate, the buffer concentration is 0.02 M. Generally, while not intending to be limiting, in an ophthalmic composition, the buffer concentration can be up to about 0.2 M. Some compositions comprise from 0 to 50 mM buffer. Other compositions comprise from 5 to 15 mM buffer. Still other compositions comprise from 0 to 10 mM buffer. Other compositions comprise about 10 mM buffer.

Another commonly used excipient in ophthalmic compositions is a viscosity-enhancing, or a thickening agent. Thickening agents are used for a variety of reasons, ranging from improving the form of the formulation for convenient administration to improving the contact with the eye to improve bioavailability. The viscosity-enhancing agent may comprise a polymer containing hydrophilic groups such as monosaccharides, polysaccharides, ethylene oxide groups, hydroxyl groups, carboxylic acids or other charged functional groups. While not intending to limit the scope of the invention, some examples of useful viscosity-enhancing agents are sodium carboxymethylcellulose, hydroxypropylmethylcellulose, povidone, polyvinyl alcohol, and polyethylene glycol.

In ophthalmic solutions, tonicity agents often are used to adjust the composition of the formulation to the desired isotonic range. Tonicity agents are well known in the art and some examples include glycerin, mannitol, sorbitol, sodium chloride, and other electrolytes.

Another composition consists essentially of from 0.6 to 1.8% prednisolone acetate, from 10% to 25% hydroxypropyl-γ-cyclodextrin, from 0% to 0.25% hydroxypropylmethylcellulose, from 3 to 10 ppm PHMB, from 0.05% to 0.6% sorbic acid, from 0% to 0.1% EDTA disodium, from 0 to 50 mM buffer, and a tonicity agent, with the remaining part of said composition being water, wherein said composition has a pH of from 4.5 to 5.5.

Another composition consists essentially of from 0.8 to 1.2% prednisolone acetate, from 20% to 25% hydroxypropyl-γ-cyclodextrin, from 0% to 0.12% hydroxypropylmethylcellulose, from 3 to 5 ppm PHMB, from 0.1% to 0.6% sorbic acid, from 0 to 10 mM buffer, about 0.1% EDTA disodium, and a tonicity agent, with the remaining part of said composition being water, wherein said composition has a pH of about 4.8.

EXAMPLE 1

Samples 1–20 were prepared having the components of Table 1 in addition to 1.2% Prednisolone Acetate, 25% Hydroxypropyl-gamma-cyclodextrin [Cavasol W8 HP, Wacker, Germany], 0.12% HPMC [Methocel, Dow Chemical Company, Midland, Mich.], 10 mM (pH 4.8) Acetic Acid/Na Acetate, and 0.1% EDTA in 100 Purified Water according to the following procedure.

Hydroxypropylmethylcellulose (HPMC) was slowly added to water at a temperature of 40° C. with propeller mixing. The heat was removed, and mixing continued while the solution was allowed to cool to room temperature. All of the other excipients except HP-γ-cyclodextrin and prednisolone acetate were added to the HPMC solution or pure water, and the mixture was stirred until all solids were completely dissolved. HP-γ-cyclodextrin (HPγCD) was added, and the mixture was stirred until the HPγCD was completely dissolved. Prednisolone acetate was added, and the mixture was stirred for a few minutes. The entire solution was autoclaved at 120° C. for 20 minutes. Stirring continued at room temperature upon removing the solution from the autoclave. The pH was then adjusted by the addition of HCl and/or NaOH before addition of PHMB, and the solution was filtered through a 0.45 µm cellulose acetate membrane.

A brief description of the test procedure is as follows: *Staphylococcus aureus* ATCC 6538, *Pseudomonas aeruginosa* ATCC 9027, *Escherichia coli* ATCC 8739, *Candida albicans* ATCC 10231 and *Aspergillus niger* ATCC 16404 were evaluated as the challenge organisms. For each organism, ten milliliters of product were dispensed into a polystyrene test tube. Sample tubes were then inoculated to contain approximately $1 \times 10^5$ to $1 \times 10^6$ colony-forming units (CFU) per mL of one of the five challenge organisms. Sample tubes were then vortexed and stored at 22.5±2.5° C. Standard 1-mL aliquots of each sample tube were assayed at 6 hours, 24 hours, 7 days, 14 days and 28 days to determine the numbers of viable CFU per mL. Removed aliquots were neutralized in Leethen broth followed by performing standard plate counts. *Candida albicans* and *Aspergillus niger* were not evaluated at 6 and 24 hours.

The criteria for passing antimicrobial preservative effectiveness can be found in USP-NF and European Pharmacopoeias, and are summarized in Table 1a below.

TABLE 1a

USP, Ph Eur-A, and Ph Eur-B Antimicrobial Preservative Efficacy Test Criteria

| Organism | USP | Ph Eur-A | Ph Eur-B |
|---|---|---|---|
| S. aureus ATCC 6538 | 1.0 log at 7 days | 2 logs at 6 hours | 1 log at 24 hours |
| P. aeruginosa ATCC 9027 | 3.0 logs at 14 days | 3 logs at 24 hours | 3 logs at 7 days |
| E. coli ATCC 8739 | | No recovery at 28 days | |
| C. albicans ATCC 10231 | Stasis | 2 logs at 7 days | 1 log at 14 days |
| A. niger ATCC 16404 | | | |

E. coli is not required to be evaluated by Ph Eur-A/B criteria. All criteria stipulate no increase after the required reductions.

TABLE 1b

| Sample | S. aureus ATCC 6538 | P. aeruginosa ATCC 9027 | E. coli ATCC 8739 | C. albicans ATCC 10231 | A. niger ATCC 16404 |
|---|---|---|---|---|---|
| #1<br>2 ppm PHMB,<br>0.6% Boric Acid,<br>0.5% Glycerol | Pass USP<br>Fail Ph Eur-A<br>Fail Ph Eur-B | Pass USP<br>Fail Ph Eur-A<br>Pass Ph Eur-B | Pass USP | Pass USP<br>Pass Ph Eur-A<br>Pass Ph Eur-B | Pass USP<br>Fail Ph Eur-A<br>Fail Ph Eur-B |
| #2<br>3 ppm PHMB,<br>0.6% Boric Acid,<br>0.5% Glycerol | Pass USP<br>Pass Ph Eur-A<br>Pass Ph Eur-B | Pass USP<br>Pass Ph Eur-A<br>Pass Ph Eur-B | Pass USP | Pass USP<br>Pass Ph Eur-A<br>Pass Ph Eur-B | Pass USP<br>Fail Ph Eur-A<br>Pass Ph Eur-B |
| #3<br>3 ppm PHMB,<br>No Boric Acid,<br>0.5% Glycerol | Pass USP<br>Pass Ph Eur-A<br>Pass Ph Eur-B | Pass USP<br>Pass Ph Eur-A<br>Pass Ph Eur-B | Pass USP | Pass USP<br>Pass Ph Eur-A<br>Pass Ph Eur-B | Pass USP<br>Fail Ph Eur-A<br>Fail Ph Eur-B |
| #4<br>3 ppm PHMB,<br>0.6% Boric Acid,<br>No Glycerol | Pass USP<br>Pass Ph Eur-A<br>Pass Ph Eur-B | Pass USP<br>Pass Ph Eur-A<br>Pass Ph Eur-B | Pass USP | Pass USP<br>Pass Ph Eur-A<br>Pass Ph Eur-B | Pass USP<br>Fail Ph Eur-A<br>Fail Ph Eur-B |
| #5<br>4 ppm PHMB,<br>0.6% Boric Acid,<br>0.5% Glycerol | Pass USP<br>Pass Ph Eur-A<br>Pass Ph Eur-B | Pass USP<br>Pass Ph Eur-A<br>Pass Ph Eur-B | Pass USP | Pass USP<br>Pass Ph Eur-A<br>Pass Ph Eur-B | Pass USP<br>Fail Ph Eur-A<br>Fail Ph Eur-B |
| #6<br>5 ppm PHMB,<br>0.6% Boric Acid,<br>0.5% Glycerol | Pass USP<br>Pass Ph Eur-A<br>Pass Ph Eur-B | Pass USP<br>Pass Ph Eur-A<br>Pass Ph Eur-B | Pass USP | Pass USP<br>Pass Ph Eur-A<br>Pass Ph Eur-B | Pass USP<br>Fail Ph Eur-A<br>Fail Ph Eur-B |
| #7<br>8 ppm PHMB,<br>0.6% Boric Acid,<br>0.5% Glycerol | Pass USP<br>Pass Ph Eur-A<br>Pass Ph Eur-B | Pass USP<br>Pass Ph Eur-A<br>Pass Ph Eur-B | Pass USP | Pass USP<br>Pass Ph Eur-A<br>Pass Ph Eur-B | Pass USP<br>Fail Ph Eur-A<br>Fail Ph Eur-B |
| #8<br>10 ppm PHMB,<br>0.6% Boric Acid,<br>0.5% Glycerol | Pass USP<br>Pass Ph Eur-A<br>Pass Ph Eur-B | Pass USP<br>Pass Ph Eur-A<br>Pass Ph Eur-B | Pass USP | Pass USP<br>Pass Ph Eur-A<br>Pass Ph Eur-B | Pass USP<br>Fail Ph Eur-A<br>Fail Ph Eur-B |
| #9<br>2 ppm PHMB,<br>0.6% Sorbic Acid,<br>0.5% Glycerol | Pass USP<br>Fail Ph Eur-A<br>Pass Ph Eur-B | Pass USP<br>Pass Ph Eur-A<br>Pass Ph Eur-B | Pass USP | Pass USP<br>Pass Ph Eur-A<br>Pass Ph Eur-B | Pass USP<br>Pass Ph Eur-A<br>Pass Ph Eur-B |
| #10<br>3 ppm PHMB,<br>0.6% Sorbic Acid,<br>0.5% Glycerol | Pass USP<br>Pass Ph Eur-A<br>Pass Ph Eur-B | Pass USP<br>Pass Ph Eur-A<br>Pass Ph Eur-B | Pass USP | Pass USP<br>Pass Ph Eur-A<br>Pass Ph Eur-B | Pass USP<br>Pass Ph Eur-A<br>Pass Ph Eur-B |
| #11<br>3 ppm PHMB,<br>No Sorbic Acid,<br>No Glycerol | Pass USP<br>Pass Ph Eur-A<br>Pass Ph Eur-B | Pass USP<br>Pass Ph Eur-A<br>Pass Ph Eur-B | Pass USP | Pass USP<br>Pass Ph Eur-A<br>Pass Ph Eur-B | Pass USP<br>Fail Ph Eur-A<br>Fail Ph Eur-B |
| #12<br>3 ppm PHMB,<br>0.6% Sorbic Acid,<br>No Glycerol | Pass USP<br>Pass Ph Eur-A<br>Pass Ph Eur-B | Pass USP<br>Pass Ph Eur-A<br>Pass Ph Eur-B | Pass USP | Pass USP<br>Pass Ph Eur-A<br>Pass Ph Eur-B | Pass USP<br>Pass Ph Eur-A<br>Pass Ph Eur-B |
| #13<br>4 ppm PHMB,<br>0.6% Sorbic Acid,<br>0.5% Glycerol | Pass USP<br>Pass Ph Eur-A<br>Pass Ph Eur-B | Pass USP<br>Pass Ph Eur-A<br>Pass Ph Eur-B | Pass USP | Pass USP<br>Pass Ph Eur-A<br>Pass Ph Eur-B | Pass USP<br>Pass Ph Eur-A<br>Pass Ph Eur-B |
| #14<br>5 ppm PHMB,<br>0.6% Sorbic Acid,<br>0.5% Glycerol | Pass USP<br>Pass Ph Eur-A<br>Pass Ph Eur-B | Pass USP<br>Pass Ph Eur-A<br>Pass Ph Eur-B | Pass USP | Pass USP<br>Pass Ph Eur-A<br>Pass Ph Eur-B | Pass USP<br>Pass Ph Eur-A<br>Pass Ph Eur-B |
| #15<br>8 ppm PHMB, | Pass USP<br>Pass Ph Eur-A | Pass USP<br>Pass Ph Eur-A | Pass USP | Pass USP<br>Pass Ph Eur-A | Pass USP<br>Pass Ph Eur-A |

TABLE 1b-continued

| Sample | S. aureus ATCC 6538 | P. aeruginosa ATCC 9027 | E. coli ATCC 8739 | C. albicans ATCC 10231 | A. niger ATCC 16404 |
|---|---|---|---|---|---|
| 0.6% Sorbic Acid, 0.5% Glycerol | Pass Ph Eur-B | Pass Ph Eur-B | | Pass Ph Eur-B | Pass Ph Eur-B |
| #16 10 ppm PHMB, 0.6% Sorbic Acid, 0.5% Glycerol | Pass USP Pass Ph Eur-A Pass Ph Eur-B | Pass USP Pass Ph Eur-A Pass Ph Eur-B | Pass USP | Pass USP Pass Ph Eur-A Pass Ph Eur-B | Pass USP Pass Ph Eur-A Pass Ph Eur-B |
| #17 100 ppm BAK, 0.6% Boric Acid, 0.5% Glycerol | Pass USP Fail Ph Eur-A Fail Ph Eur-B | Pass USP Pass Ph Eur-A Pass Ph Eur-B | Pass USP | Pass USP Fail Ph Eur-A Pass Ph Eur-B | Pass USP Fail Ph Eur-A Pass Ph Eur-B |
| #18 150 ppm BAK, 0.6% Boric Acid, 0.5% Glycerol | Pass USP Fail Ph Eur-A Fail Ph Eur-B | Pass USP Pass Ph Eur-A Pass Ph Eur-B | Pass USP | Pass USP Fail Ph Eur-A Pass Ph Eur-B | Pass USP Fail Ph Eur-A Pass Ph Eur-B |
| #19 200 ppm BAK, 0.6% Boric Acid, 0.5% Glycerol | Pass USP Fail Ph Eur-A Fail Ph Eur-B | Pass USP Pass Ph Eur-A Pass Ph Eur-B | Pass USP | Pass USP Fail Ph Eur-A Pass Ph Eur-B | Pass USP Fail Ph Eur-A Pass Ph Eur-B |
| #20 200 ppm BAK, No Boric Acid, No % Glycerol | Pass USP Fail Ph Eur-A Fail Ph Eur-B | Pass USP Pass Ph Eur-A Pass Ph Eur-B | Pass USP | Pass USP Fail Ph Eur-A Fail Ph Eur-B | Pass USP Fail Ph Eur-A Pass Ph Eur-B |

While not intending to be bound or limited in any way by theory, comparison of the data (Table 1b) for compositions 1–8 with that of compositions 17–20 unexpectedly shows that 100–200 ppm of benzalkonium chloride (BAK) is significantly less effective than 3–10 ppm PHMB at preserving the formulation against *S. aureus*, as the BAK formulation failed both European tests. Similarly, the PHMB formulation is also clearly superior to the BAK formulation in preserving the formulation against *C. albicans*, as the PHMB formulation passed all of the tests, whereas the BAK formulation failed the Ph Eur-B tests. Thus, while not intending to limit the scope of the invention in any way, or be bound by theory, it appears that PHMB is superior to BAK in preserving ophthalmic compositions.

While not intending to limit the scope of the invention in any way, although PHMB is clearly superior to BAK overall in preserving ophthalmic formulations, it appears that PHMB is somewhat less effective than BAK in the case of *A. niger*. Surprisingly, the data for compositions 9–16 clearly shows the replacement of boric acid with sorbic acid corrects this deficiency, such that the PHMB/sorbate combination are effective against all of the tested pathogens in all of the tests when the concentration of PHMB is 3 ppm or greater.

What is claimed is:

1. A composition comprising a cyclodextrin, a guanidine-based cationic compound, and sorbic acid, wherein said composition is an ophthalmic liquid.

2. The composition of claim 1 comprising a therapeutically active agent.

3. The composition of claim 1 comprising PHMB.

4. The composition of claim 1 comprising chlorhexidine.

5. The composition of claim 1 comprising a cyclodextrin selected from the group consisting of β-cyclodextrin, γ-cyclodextrin, hydroxypropyl-β-cyclodextrin, hydroxypropyl-γ-cyclodextrin, sulfobutylether-β-cyclodextrin, and sulfobutylether-γ-cyclodextrin.

6. The composition of claim 2 wherein the therapeutically active agent is selected from the group consisting of prostaglandins, prostamides, retinoids, α-adrenergic agonists, tyrosine kinase inhibitors, and steroids.

7. The composition of claim 2 wherein the therapeutically active agent is selected from the group consisting of prednisolone, prednisone, androgens, estrogens, glucocorticoids, progestins, mineralocorticoids, and corticosteroids.

8. The composition of claim 2 wherein the therapeutically active agent is selected from the group consisting of cortisone, hydrocortisone, prednisone, prednisolone, methylprednisone, triamcinolone, fluorometholone, dexamethasone, medrysone, betamethasone, loteprednol, fluocinolone, flumethasone, mometasone, testosterone, methyltestosterone, and danazol.

9. The composition of claim 2 consisting essentially of from 0.6 to 1.8% prednisolone acetate, from 10% to 25% hydroxypropyl-γ-cyclodextrin, from 0% to 0.25% hydroxypropylmethylcellulose, from 3 to 10 ppm PHMB HCl, from 0.05% to 0.6% sorbic acid, from 0% to 0.1% EDTA disodium, from 0 to 50 mM buffer, and a tonicity agent, with the remaining part of said composition being water, wherein said composition has a pH of from 4.5 to 5.5.

10. The composition of claim 2 consisting essentially of from 0.8 to 1.2% prednisolone acetate, from 20% to 25% hydroxypropyl-γ-cyclodextrin, from 0% to 0.12% hydroxypropylmethylcellulose, from 3 to 5 ppm PHMB HCl, from 0.1% to 0.6% sorbic acid, from 0 to 10 mM buffer, about 0.1% EDTA disodium, and a tonicity agent, with the remaining part of said composition being water, wherein said composition has a pH of about 4.8.

11. The composition of claim 1 wherein the concentration of the guanidine-based cationic compound is from 0.1 ppm to 25 ppm.

12. A preservative for cyclodextrin-containing ophthalmic compositions comprising a guanidine-based cationic compound and sorbic acid.

13. The preservative of claim 12 wherein said composition comprises a water-insoluble therapeutically active agent.

14. The preservative of claim 12 comprising PHMB.

15. The preservative of claim 12 comprising chlorhexidine.

16. The composition of claim 1 comprising from 3 ppm to 5 ppm PHMB HCl.

17. The composition of claim 16 comprising from 0.05% to 1% sorbic acid.

18. The composition of claim 17 comprising about 0.6% sorbic acid.

19. The composition of claim 1 wherein the concentration of the cyclodextrin is from 10% to 30%.

20. The composition of claim 1 wherein the pH is from 4 to 6.

21. A method of preventing, attenuating, or reducing the pathogenic contamination of an ophthalmic composition by adding to said ophthalmic composition a composition comprising a cyclodextrin with an effective amount of a guanidine-based cationic compound and an effective amount of sorbic acid.

22. The method of claim 21 wherein said guanidine-based cationic compound is PHMB.

23. The composition of claim 1 wherein the composition of the guanidine-based cationic compound is about 3 ppm or greater.

\* \* \* \* \*